(12) United States Patent
Bayer et al.

(10) Patent No.: US 9,486,337 B2
(45) Date of Patent: Nov. 8, 2016

(54) IMPLANT AND METHOD FOR PRODUCING THE SAME

(71) Applicant: BIOTRONIK AG, Buelach (CH)

(72) Inventors: Ullrich Bayer, Admannshagen-Bargeshagen (DE); Bernd Block, Rostock (DE); Daniel Lootz, Rostock (DE); Jan Hannemann, Rostock (DE); Nils Venohr, Rostock (DE)

(73) Assignee: BIOTRONIK AG, Buelach (CH)

( * ) Notice: Subject to any disclaimer, the term of this patent is extended or adjusted under 35 U.S.C. 154(b) by 489 days.

(21) Appl. No.: 13/862,888

(22) Filed: Apr. 15, 2013

(65) Prior Publication Data

US 2013/0282104 A1 Oct. 24, 2013

Related U.S. Application Data

(60) Provisional application No. 61/636,742, filed on Apr. 23, 2012.

(51) Int. Cl.
| | |
|---|---|
| *B21C 37/15* | (2006.01) |
| *A61F 2/82* | (2013.01) |
| *A61L 31/02* | (2006.01) |
| *A61L 31/14* | (2006.01) |
| *B21K 23/00* | (2006.01) |

(Continued)

(52) U.S. Cl.
CPC .............. *A61F 2/82* (2013.01); *A61L 31/022* (2013.01); *A61L 31/148* (2013.01); *B21C 23/085* (2013.01); *B21C 33/004* (2013.01); *B21C 37/154* (2013.01); *B21K 23/00* (2013.01); *Y10T 29/49945* (2015.01)

(58) Field of Classification Search
CPC .......... B21C 1/003; B21C 1/16; B21C 1/18; B21C 1/22; B21C 23/01; B21C 23/08; B21C 23/085; B21C 33/004; B21C 37/154
See application file for complete search history.

(56) References Cited

U.S. PATENT DOCUMENTS

| | | | |
|---|---|---|---|
| 5,858,556 A | 1/1999 | Eckert et al. | |
| 5,958,602 A * | 9/1999 | Usui | B21C 37/06 138/142 |
| 5,988,484 A | 11/1999 | Osborn et al. | |

(Continued)

FOREIGN PATENT DOCUMENTS

| | | |
|---|---|---|
| DE | 10301850 A1 | 7/2004 |
| EP | 2332588 A2 | 6/2011 |

(Continued)

*Primary Examiner* — Debra Sullivan
(74) *Attorney, Agent, or Firm* — Wagenknecht IP Law Group PC

(57) ABSTRACT

A method for producing a semifinished part (20) for an implant, in particular for an intraluminal endoprosthesis, which comprises the following steps:
  a) providing a first sleeve (11) from a first metallic material and at least one second sleeve (12, 13) from a second metallic material,
  b) arranging the first sleeve (11) and the at least one second sleeve (12, 13) into one another in such a manner that the sleeve combination (10) forms at least a press fit between said sleeves, and
  c) forming the sleeve combination (10) at an increased temperature by means of extrusion.

The invention further includes a method for producing an implant, to a corresponding semifinished part or a corresponding implant, respectively.

10 Claims, 4 Drawing Sheets

(51) Int. Cl.
   *B21C 23/08*   (2006.01)
   *B21C 33/00*   (2006.01)

(56) References Cited

U.S. PATENT DOCUMENTS 6,050,301 A * 4/2000 Yoshida .................. B21C 23/22
138/142

2011/0144761 A1   6/2011   Rzany et al.
2012/0125070 A1   5/2012   Birgmann et al.

FOREIGN PATENT DOCUMENTS

| WO | 9831304 A1 | 7/1998 |
| WO | 9951370 A1 | 10/1999 |
| WO | 2010132910 A1 | 11/2010 |

* cited by examiner

IMPLANT AND METHOD FOR PRODUCING THE SAME

CROSS REFERENCE TO RELATED APPLICATIONS

This application claims benefit of priority to U.S. provisional patent application Ser. No. 61/636,742 filed Apr. 23, 2012; the content of which is herein incorporated by reference in its entirety.

TECHNICAL FIELD

The invention relates to a method for producing a semifinished part for an implant, in particular for an intraluminal endoprosthesis, and to a method for producing such an implant, and to a corresponding semifinished part or implant.

BACKGROUND

Medical endoprostheses or implants for a wide range of applications are known in a large variety from the prior art. Implants in the meaning of the present invention are to be understood as endovascular prostheses or other endoprostheses, for example stents, orthopedic implants, e.g. fastener elements for bones, for example screws, plates or nails, surgical sutures, intestinal staples, vascular clips, prostheses in the region of the hard and soft tissue, and anchor elements for electrodes, in particular of pacemakers or defibrillators.

Today, particularly frequently used as implants are stents which serve for the treatment of stenoses (vasoconstrictions). Stents have a body in the form of a tubular or hollow cylindrical basic grid which is open at both longitudinal ends. As an initial shape for such a body, hollow-cylindrical semifinished parts are usually used from which subsequently the basic grid is cut out, for example by means of laser.

Such an endoprosthesis having a tubular grid is inserted into the vessel to be treated and serves for supporting the vessel. Stents have established themselves in particular for the treatment of vascular diseases. By using stents, constricted regions in the vessels can be expanded resulting in a lumen gain. By using stents or other implants, an optimal vascular cross-section primarily necessary for the success of the therapy can be achieved; however, the permanent presence of such a foreign body initiates a cascade of microbiological processes which can result in a gradual blocking of the stent and in the worst case in a vascular occlusion.

SUMMARY

One approach for the solution of this problem is to produce the stent or other implants from a biodegradable material.

Biodegradation is to be understood as hydrolytic, enzymatic and other metabolic-related degradation processes in a living organism which are mainly caused by body liquids which contact the biodegradable material of the implant and which result in a gradual degradation of the structures of the implant containing the biodegradable material. Through this process, the implant loses its mechanical integrity at a certain point in time. As a synonym for the term biodegradation, the term biocorrosion is frequently used. The term bioresorption refers to the subsequent resorption of the degradation products by the living organism.

Suitable materials for the body of biodegradable implants can contain, for example, polymers or metals. The body can include of a plurality of the materials. A common feature of the materials is their biodegradability. Examples of suitable polymeric compounds are polymers selected from the group of cellulose, collagen, albumin, casein, polysaccharides (PSAC), polyactide (PLA), poly-L-lactide (PLLA), polyglycol (PGA), poly-D,L-lactide-co-glycolide, (PDLLA-PGA), polyhydroxybutyrate (PHB), polyhydroxyvaleric acid (PHV), polyalkyle carbonate, polyorthoester, polyethylene terephthalate (PET), polymalonic acid (PML), polyanhydrides, polyphosphazenes, polyamino acids and their co-polymers, and hyaluronic acid. Depending on the desired properties, the polymers can be available in pure form, in derivatized form, in the form of blends, or as co-polymers. The present invention relates to implants made of a metallic biodegradable material, in particular based on magnesium or a magnesium alloy.

Already known are stents which have coatings with different functions. Such coatings serve, for example, for releasing drugs, arranging an x-ray marker, or for protecting the underlying structures.

When implementing biodegradable implants, the degradability is to be controlled according to the intended therapy or the application of the respective implant (coronary, intracranial, renal, etc.). For many therapeutic applications, an important target corridor is, for example, that the implant loses its integrity within a time period of four weeks to six months. Here, integrity, i.e., mechanical integrity, is to be understood as the property that the implant barely experiences any mechanical shortcomings with respect to the nondegradable implant. This means that the implant is still mechanically stable such that, for example, the collapse pressure has dropped only insignificantly, i.e., not below 80% of the nominal value. Thus, with existing integrity, the implant still meets its main function which is to keep the vessel open. Alternatively, integrity can be defined in that the implant is mechanically stable such that it is barely subject of any geometrical changes in its loaded state in the vessel, for example, does not collapse significantly, i.e., shows under load at least 80% of the dilatation diameter or, in case of a stent, has barely any partially fractured supporting struts.

It was found that biodegradable magnesium implants, in particular magnesium stents, are particularly promising for the mentioned target corridor of the degradation; however, on the one hand, they lose their mechanical integrity or supporting effect still too early and, on the other, they show a significantly fluctuating integrity loss in vitro and in vivo. This means that in the case of magnesium stents, the collapse pressure over time decreases too rapidly or, respectively, the decrease of the collapse pressure has a variability that is too high and therefore is not sufficiently determinable.

In the prior art, different mechanisms for controlling degradation of implants have already been described. They are based, for example, on inorganic or organic protective layers or their combinations which resist the human corrosive environment and the corrosion processes taking place therein. Previously known solutions are characterized in that barrier layer effects are achieved which are based on a spatial and preferably defect-free separation of the corrosion medium from the metallic material, in particular the metallic magnesium. Thus, the degradation protection is ensured through differently composed protective layers and by defined geometrical distances (diffusion barriers) between the corrosion medium and the basic magnesium material. Further solutions in the field of controlled degradation result in the effect of predetermined breaking points caused by implementing physical (e.g. local changes in cross-section)

and/or chemical changes of the stent surface (e.g. multilayers which are locally different with regard to their chemical composition).

Another problem in connection with coatings arises from the fact that stents or implants normally assume two different states, namely a compressed state with a small diameter and an expanded state with a larger diameter. In the compressed state, the implant can be inserted by means of a catheter into the vessel to be supported and can be positioned at the position to be treated. At the site of treatment, the implant is then dilated, for example by means of a balloon catheter. Due to the diameter change, the body of the implant is subjected here to a mechanical load. Further mechanical loads on the implants can occur during the production of the implant or during movement of the implant in or with the vessel in which the implant is inserted. The above-mentioned coatings according to the prior art thus have the disadvantage that the coating breaks during the deformation of the implant (e.g. formation of micro cracks) or is partially removed. Hereby, an unspecified local degradation can be caused. Moreover, the start and the speed of the degradation depend on the size and the distribution of the micro-cracks generated by the deformation, which, as defects, are difficult to control. This results in a high variance of the degradation times.

Further examples for known organic or inorganic protective layers for increasing the degradation resistance are galvanic coatings by means of zinc, coatings based on ionic liquids, conversion layers through chemical conversion of the main alloying constituents, vaporizing or sputtering with aluminum, thermal spraying and the like, which, however, result only in protective layers of very limited thickness (few µm).

Furthermore, high-alloy base materials are used for improving the degradation resistance. From the printed matter WO 2011/051424 A1, an implantable medical device is known which consists at least partially of a material that contains high-purity magnesium or a magnesium alloy with high-purity magnesium and one or a plurality of further high-purity alloying constituents. High-purity alloying constituents can be the elements indium, scandium, yttrium, gallium and the rare earths. Producing such high-purity materials is very expensive so that also the costs for a medical instrument produced therefrom is high.

The publication EP 2 332 588 describes the contacting of a base body from magnesium or a biodegradable magnesium alloy with a corrosion-inhibiting element selected from the group Al, Zn, Ca, Si, In, Mn, Sc and RE (RE stands for rare earths), and a subsequent thermal treatment. As a result of this method, a diffusion layer covering the base body is formed in the region of the contact surface. The mentioned elements diffuse into the surface of the implant, namely up to a depth of approximately 20 µm. The penetration depth of the respective elements is determined by the diffusion coefficient in the magnesium matrix. This known solution is therefore also very limited with regard to the thickness of the anti-corrosion layer so that the use of these technologies make sense only on finish-processed implants. Otherwise, such a diffusion layer would be removed again for the most part through downstream processes such as reaming, etching or electrolytic polishing.

Moreover, in order to reach the range of mutual solubility of the materials used, the known solutions often require a tempering treatment at temperatures above 450° C. (better above 500° C.). However, in this temperature range, a grain growth takes place in the magnesium material which negatively influences the mechanical behavior of the implant, in particular the forming behavior of the latter.

The known solutions therefore have the following disadvantages:

1. Magnesium implants without surface treatment have a degradation speed which is too high.
2. The resistance against crack formation and strut fracture during the dilation of stents made of magnesium alloys is low due to the magnesium's hexagonal microstructure which has a low deformability at body temperature.
3. Possible applicable technologies for treating the surface of implants with aluminum or zinc layers, namely sputtering, vaporizing or a treatment in ionic liquids, are costly and the adhesion on the magnesium basis of the layer produced in this manner is low.
4. All subsequent treatment steps on filigree implants such as stents are disadvantageously from a production-related view because due to the additional handling of the implants in a further process step, mechanical deformations of the components occur more frequently resulting in an increased rejection rate.
5. High-alloy base materials (e.g. Mg with an alloy proportion of rare earths of more than 10% by weight) which have an increased degradation resistance have the disadvantage that they have rather poor mechanical properties, in particular a low elongation at break.
6. When using high-alloy base materials, precipitates (inclusions) caused by the alloy are generated during the production, which precipitates result in inhomogeneities in the mechanical and chemical properties and thereby cause a high variation in the mechanical properties.
7. Conventionally-produced semifinished parts (e.g. by means of cladding methods in the case of sheet metals) frequently show delamination of the layer from the magnesium base body during the deformation of the final product produced from said semifinished parts, e.g. during the dilation of stents.
8. Methods using thermal finishing treatments of semifinished parts or implants which are coated with foreign metals such as aluminum or zinc in order to control degradation can result in alloying the base material in the region near the surface. However, this region is limited to few µm with regard to its depth.

It is therefore an object of the present invention to provide a cost-effective method for producing a semifinished part or an implant, which method achieves a degradation delay and does not have the aforementioned disadvantages. Accordingly, it is also an object of the invention to provide such a semifinished part or implant.

The above-mentioned object is achieved by the method with the features of the claim 1 and the claim 9.

The method for producing a semifinished part for an implant comprises in particular the following steps:

a) Providing a first sleeve from a first metallic material and at least one second sleeve from a second metallic material, b) Arranging the first sleeve and the at least one second sleeve into one another in such a manner that this sleeve combination forms a press fit between the sleeves, c) Forming the sleeve combination at an increased temperature by means of extrusion.

The method according to the invention is based on the knowledge that by using at least two tubes (or hollow cylinders, hereinafter designated as sleeves) which are inserted in one another and are made from different materials which are preferably characterized by a high mutual miscibility, the tubes can be connected to each other during the forming step carried out according to the invention in the form of an extrusion (semi-hot or hot extrusion) not only via mechanical forces (press fit, e.g. a press fit with a fit tolerance in the range H7/k6, light press fit), but can also be connected through the material. Through the forming step carried out during the method according to the invention which preferably takes place at a temperature of the tool and the sleeve combination in the range from 300° C. to 500° C., depending on the materials used in each case, material gradients form in the region in which the sleeves adjoin each other because the constituents of the one material diffuse into the respective other material. Hereby, the risk of delaminations between the individual layers is reduced because material gradients form between the layers due to the thermodynamic treatment during the extrusion process, and sharp interfaces do not exist anymore. Due to the diffusion of the material constituents, the sleeves quasi interlock with each other. The method according to the invention therefore includes a thermomechanical treatment with mass transfer.

Preferably, the first sleeve contains magnesium or a magnesium alloy or is made completely from one of the two materials. For degradation control, for example, a second sleeve can be arranged on the outside of the first sleeve, said second sleeve containing an element selected from the group containing aluminum and zinc or an alloy with at least one element from said group, for example consisting of Al99,5, or ZnAl4. A third sleeve made from one of the mentioned materials for degradation control can in addition also be arranged within the first sleeve.

If the above-mentioned materials are used in the outer sleeves, due to the enrichment of the implant surface with these materials, the electrochemical potential is shifted toward higher values with respect to an implant made from a magnesium alloy. This results in a decelerated degradation speed.

Depending on the composition of the sleeves used for the method according to the invention, a lower ph value increase can be set due to the lower magnesium content and the sleeves' corrosion products in cell contact so that the degradation mechanism with respect to a polymer coating which potentially lies on the layer of the semifinished part, which layer has been formed by the sleeve arranged farthest on the outside, can be positively influenced.

Another great advantage of the method according to the invention is that the wall thickness of the tubes used for the sleeve combination and also their length can be varied within a very wide range through the process parameters during the extrusion process and its subsequent treatment.

The implants made from the semifinished parts produced with the method according to the invention are characterized by improved mechanical properties during dilatation (reduced susceptibility to fracture) as well as during the cyclical load during the clinical use due to a reduced susceptibility with respect to surface-defect-induced cracks and due to considerably improved corrosion properties.

The reason for this is that the method according to the invention allows producing anticorrosion layers which have a significantly greater layer thickness compared to the abovementioned conventional coating methods. This has also an effect on the lifetime so that, e.g. a stent, which consists on its outer surface of an aluminum alloy and in its inner surface of a magnesium alloy, has double the lifetime compared to an identical implant produced from a magnesium alloy.

As a test medium for examining the corrosion behavior serves, for example, artificial plasma which is specified according to EN ISO 10993-15:2000 for bio corrosion tests (composition NaCl 6.8 g/l, $CaCl_2$, 0.2 g/l, KCl 0.4 g/l, $MgSO_4$ 0.1 g/l, $NaHCO_3$ 2.2 g/l, $Na_2HPO_4$ 0.126 g/l, $NaH_2PO_4$ 0.026 g/l). Samples of the material to be examined are stored at 37° C. in a closed sample container with a defined amount of the test medium. In time intervals—adapted to the expected behavior during the biodegradation—of few hours up to several months, the samples are taken and examined in a known manner for signs of degradation. The artificial plasma according to EN ISO 10993-15:2000 corresponds to a medium similar to blood and thus represents a possibility to reproducibly simulate a physiological environment in the meaning of the invention.

Moreover, the concentration of the material hindering the corrosion can be selected to be comparatively high so that, for example, on an aluminum-rich outer surface of an implant, extended possibilities with regard to a biofunctionalization are given, e.g. through enrichment with phosphate compounds by means of plasma-chemical oxidation.

The greater mechanical robustness due to the use of a semifinished part with improved mechanical properties reduces also the rejection rate when finishing the implant.

Overall, the solution according to the invention achieves a higher mechanical and chemical resistance already in the stage of the semifinished part which has no filigree structures yet so that the damage tolerance of the overall system is increased. Thus, e.g., the notch effect of an intermetallic inclusion arranged in the magnesium bulk material can be minimized. Such inclusions, if located in mechanically highly loaded regions of the implant, involve a high probability for early strut fractures at the respective locations. By using the method according to the invention, the implant's peripheral regions near the surface can be formed such that they have a lower notch sensitivity.

In a preferred embodiment, the inner first sleeve, which is also designated as basis, is found from magnesium or a magnesium alloy. The second, outer sleeve contains aluminum or an aluminum alloy. In this case, easily deformable peripheral layers, in particular in the form of cubic face-centered aluminum with a plurality of slip planes, and a component interior made from magnesium or a magnesium alloy, which is more difficult to deform, are combined with each other.

This exemplary embodiment is characterized in that an increase in mechanical stability is achieved; in particular, the outer layers containing aluminum become more ductile and therefore more fracture-resistant.

In another preferred exemplary embodiment, a third sleeve is additionally arranged within the first sleeve. This means that also the inner surface of the semifinished part or the implant produced therefrom has a different composition than the basis. In a preferred exemplary embodiment, the inner third sleeve can contain zinc or a zinc alloy, particularly preferred ZnAl4. By using zinc, the biocompatibility is improved. Zinc has advantages in particular for orthopedic implants because such an implant consists of a combination of a Zn surface which accelerates bone growth and of a biodegradable basis.

In a refinement of the invention, the at least one second sleeve and/or the third sleeve are first etched and subsequently dried prior to being arranged in one another. Etching the sleeves serves for removing contamination layers, wherein for ZnAl4, for example, a 5% aqueous HF solution can be used, for Al99,5, for example, a 15% NaOH solution can be used and for the magnesium alloy WE43, for example, a 5% ethanolic $H_3PO_4$ solution can be used. Etching the sleeves is carried out over a period of approximately 1 minute, preferably at room temperature. The edged sleeves are subsequently dried, for example by means of compressed air, and are immediately pushed or pressed into each other, preferably by means of a hand-lever press. For forming the sleeve combination by means of extrusion, the sleeve combination is arranged in a substantially hollow-cylindrical die (also called extrusion bushing), the inner diameter of which decreases at the outlet of the die. The inner diameter of the die at its outlet corresponds to the outer diameter of the semifinished part formed in the die. In the inner cavity of the sleeve combination, a punch is arranged which has a mandrel protruding in the forward direction and which exerts a pressing force on the sleeve combination in the forward direction and thereby pushes the sleeve combination through the die outlet which is reduced in cross-section. By pushing the sleeve combination through the outlet of the die having the reduced cross-section, the sleeves are pressed onto each other, elongated and reduced in their outer and inner diameters. The mandrel is arranged such that it protrudes during pressing through the outlet of the die. Through its outer diameter, the mandrel determines the inner diameter of the semifinished part coming out of the outlet of the die.

Since forming is carried out at an increased temperature in the range from 300° C. to 500° C., as already explained above, diffusions of the respective material components take place at the interfaces of the sleeves which are inserted into each other so that in the region of the original interface(s), the layers of the semifinished part, which are created through the sleeves, form gradients toward the inside of the respective sleeve. Preferably, prior to the start of the extrusion, the sleeve combination is kept in the tool over several minutes at the increased temperature so that the sleeve combination reaches the temperature of the tool.

Through forming, the outer diameter of the formed semifinished part is reduced such that said diameter is not more than 60%, preferably not more than 55% of the outer diameter of the sleeve combination prior to the forming step.

Also, the entire wall thickness of the formed semifinished part is reduced with respect to the wall thickness of the sleeve combination. Preferably, the entire wall thickness of the formed semifinished part is not more than 25%, preferably not more than 20% of the entire wall thickness of the sleeve combination prior to the forming step.

The above-illustrated deformation of the semifinished part is comparatively intensive in order to destroy the existing interfaces of the different metals mechanically and thermally in such a manner that the alloy formation by means of diffusion is possible through the interfaces which then no longer exist. In the case of lower deformation degrees, the metals do not mix because the interfaces can still act as diffusion barriers.

The increased temperature and the available process time are not sufficient in this case to allow the alloy formation to proceed.

The above object is in particular also achieved by a method for producing an implant, wherein a semifinished part is produced according to the above-described method and subsequently, a desired structure, in particular a grid, is cut out of the semifinished part by means of laser. This approach is simple and is tested to get from a semifinished part to the finished implant.

As further manufacturing steps until the completion of the implant, deburring, etching, corundum blasting and/or electrolytic polishing can follow after laser cutting. These steps can result in a reduction of the layer thickness of the outer layer(s) of the semifinished part or the implant. Electrolytic polishing results in low-contamination top layers due to great material removal effects (depth effect).

The above object is also achieved with the same advantages by a semifinished part for producing an implant which can be obtained or is obtained through one of the aforementioned methods. Analogously, the above object is also achieved by an implant, preferably intraluminal endoprosthesis, which can be obtained or is obtained through the above-mentioned method for producing an implant.

Another advantage of the implant produced with the method according to the invention is that the implant has an improved biocompatibility because the chemical surface composition on the luminal and abluminal side of the implant can be adjusted with regard to the respective tissue or the body fluid.

In a refinement of the invention, after forming and prior to laser cutting, a tempering step in the temperature range between 300° C. and 500° C. is carried out for at least one minute, and the semifinished part is subsequently cooled preferably by air and preferably to room temperature. This tempering step serves for reducing internal stress inherent in the microstructure after forming. If this stress relief annealing process would not be carried out, this would result in undesirable geometrical deformations of the semifinished part which would have a negative effect on the subsequent processing steps (e.g. tumbling in the laser clamping device and associated thereto increased cutting inaccuracy during laser cutting). During the stress relief annealing process, the diffusion of the constituents of sleeves described above in connection with the forming step continues.

In addition, a polymer coating with a thickness of several μm can be arranged on the surface of the implant, which coating serves as an additional degradation protection and/or for increasing the sliding properties, or serves as an active-substance carrier. Such a polymer coating can contain, for example, parylene, e.g. parylene N, and/or PLA (polyactide), particularly preferred PLLA (poly-L-lactide), e.g. PLLA L210.

The method according to the invention can in particular also be used for producing semifinished parts in the form of wires and round rods, which can be used for producing biodegradable orthopedic implants, e.g. bone screws and nails, cerclage wires and Kirschner wires which have a lifetime adapted to the healing process and a better formability.

Accordingly, the above object is also achieved by an implant, wherein the implant body comprises magnesium or a magnesium alloy obtainable or obtained through one of the methods specified herein.

The method according to the invention, the semifinished part according to the invention and the implant according to the invention are explained hereinafter by means of examples and figures. All illustrated and/or described features form the subject matter of the invention, also independent of their combination in the claims or their backward relation.

DETAILED DESCRIPTION

First, it is to be noted that the information contained in the following description on the concentration of an element is given in mass % unless otherwise specified in the respective passage in the description.

For producing a hollow cylindrical semifinished part for an implant, for example for a stent, a tubular or hollow-cylindrical sleeve 11 made from a magnesium alloy, for example with the composition WE43 (4% Y, 2% Nd, 0.5% Gd, 0.5% Dy, 0.5% Zr, balance Mg) is first dry-machined (i.e. without lubrication) by turning it to the required length, for example a length of 8 mm. The sleeve 11 has, for example, a wall thickness of 500 µm and an outer diameter of 3.4 mm.

Analogously, a hollow-cylindrical sleeve 12 made from Al99,5 of the composition 0.25% Si, 0.4% Fe, 0.05% Cu, 0.05% Mn, 0.05% Mg, 0.07% Zn, 0.05% Ti, balance aluminum (the composition corresponds to the composition according to EN 573-3 and gives maximum contents (except for Al) in mass %) with a wall thickness of 263 µm and an outer diameter Da1 of 3.926 mm, and a hollow-cylindrical sleeve 13 made from ZnAl4 with a length of 8 mm, a wall thickness of 300 µm, an outer diameter of 2.4 mm and an inner diameter Di1 of 1.8 mm are provided.

Sleeve 11 comprises a volume of 36.411 mm$^3$, sleeve 12 comprises a volume of 24.193 mm$^3$ and sleeve 13 comprises a volume of 16.064 mm$^3$.

Figure 1:
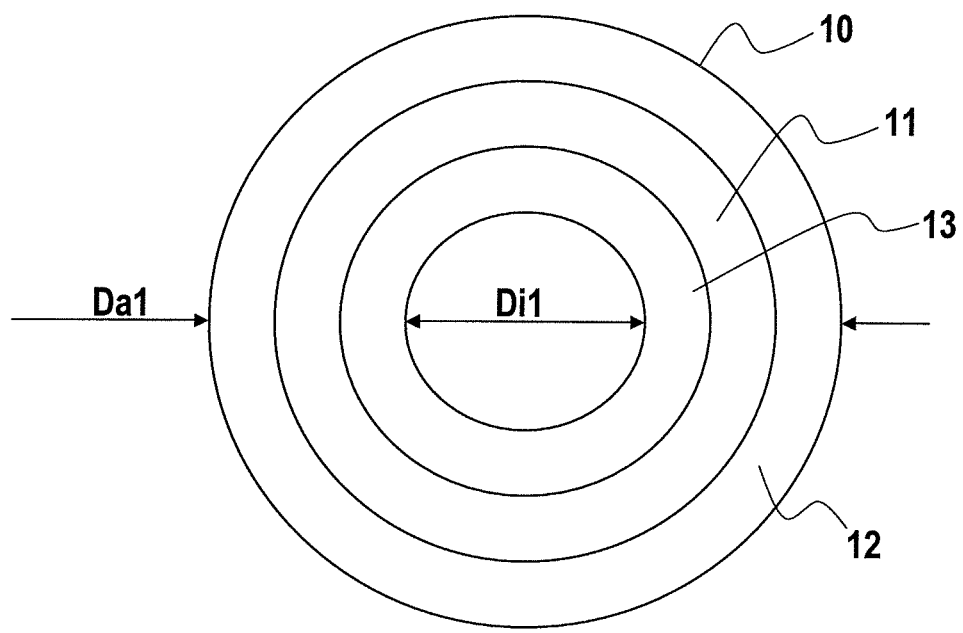
FIG. 1 shows a cross-section through a sleeve combination prior to the forming step.

Subsequently, the sleeves are etched, namely sleeve 11 in 5% ethanolic H3PO4 solution, sleeve 12 in a 15% aqueous NaOH solution and sleeve 13 in a 5% aqueous HF solution, in each case over a period of 1 minute at room temperature. The sleeves 11, 12, 13 are subsequently dried by means of compressed air and after that are pressed into one another by means of a hand-lever press so that said sleeves are arranged one inside the other as a sleeve combination 10 in the manner shown in FIG. 1. Here, sleeve 13 is first pressed into sleeve 11 and subsequently, the combination of sleeve 11 and sleeve 13 is pressed into the outer sleeve 12. The dimensions of the sleeves are configured in such a manner that between sleeve 12 and sleeve 11 and also between sleeve 11 and sleeve 13, a press fit is created in each case after the arrangement of said sleeves inside each other.

In this exemplary embodiment and the exemplary embodiments illustrated hereinafter, the press fit tolerances of the individual sleeve segments lie in the range H7/k6 (light press fit). This means that only minor forces are required for fitting the sleeves segments into each other (preferred allowance for interference is approx. 6 µm, i.e., the outer diameter of each of the respective inner sleeves can be up to 6 µm larger than the inner diameter of each of the respective outer sleeves). This causes that the roughness peaks of the two sleeve segments are squeezed into each other during the joining process. Larger allowances for interference are not to be set because otherwise, the pressing forces become too high and the sleeves get stuck into each other before they have reached their final position.

Figure 4:
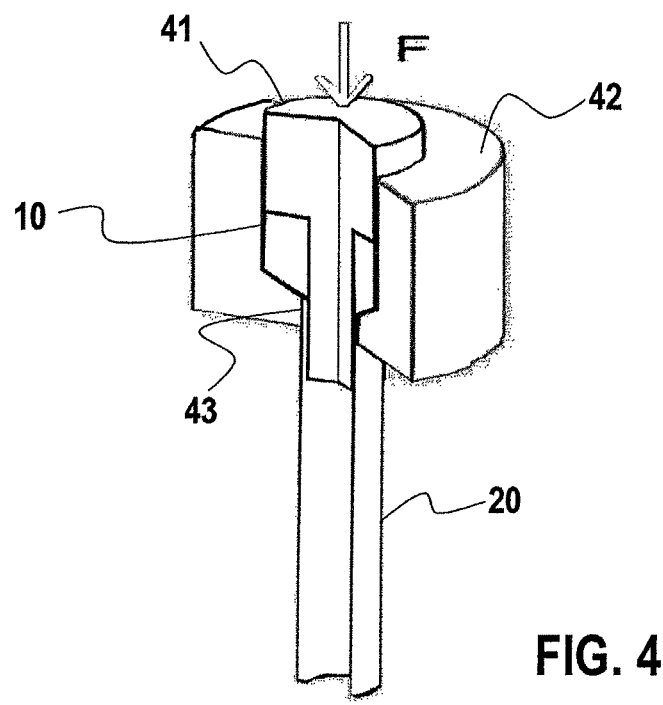
FIG. 4 shows a section through the tool used for the method according to the invention during the forming of a sleeve combination.

The sleeve combination prepared in this manner is subsequently placed into the tool shown in FIG. 4, wherein the tool has been heated in advance to a temperature between 300° C. and 500° C. Here, the sleeve combination 10 is attached on the punch 41 and placed in the die 42. Then, the sleeve combination is first kept in the tool 41, 42 for 4 minutes at temperatures between 300° C. and 500° C. Through this measure, the sleeve combination 10 is brought to a forming temperature between 300° C. and 500° C.

Subsequently, as described above, the sleeve combination is pressed by means of the punch 41 through the outlet 43 of the die 42 at a temperature between 300° C. and 500° C. and a pressing speed between 1 mm/min to 100 mm/min and a maximum pressing force F between 10 kN and 20 kN. The tool materials comprise hard metal or hardened hot-working steels.

Through forming, as described above, the dimensions of the sleeve combination is changed and at the interfaces of the sleeves 11 and 12 or 11 and 13, respectively, the above explained diffusion processes take place during which the constituents of the one sleeve diffuse in each case into the adjacent sleeve. The aforementioned volumes of the sleeves 11, 12 and 13 (now designated as layers 21, 22, 23) are not changed by the forming process.

Figure 5:
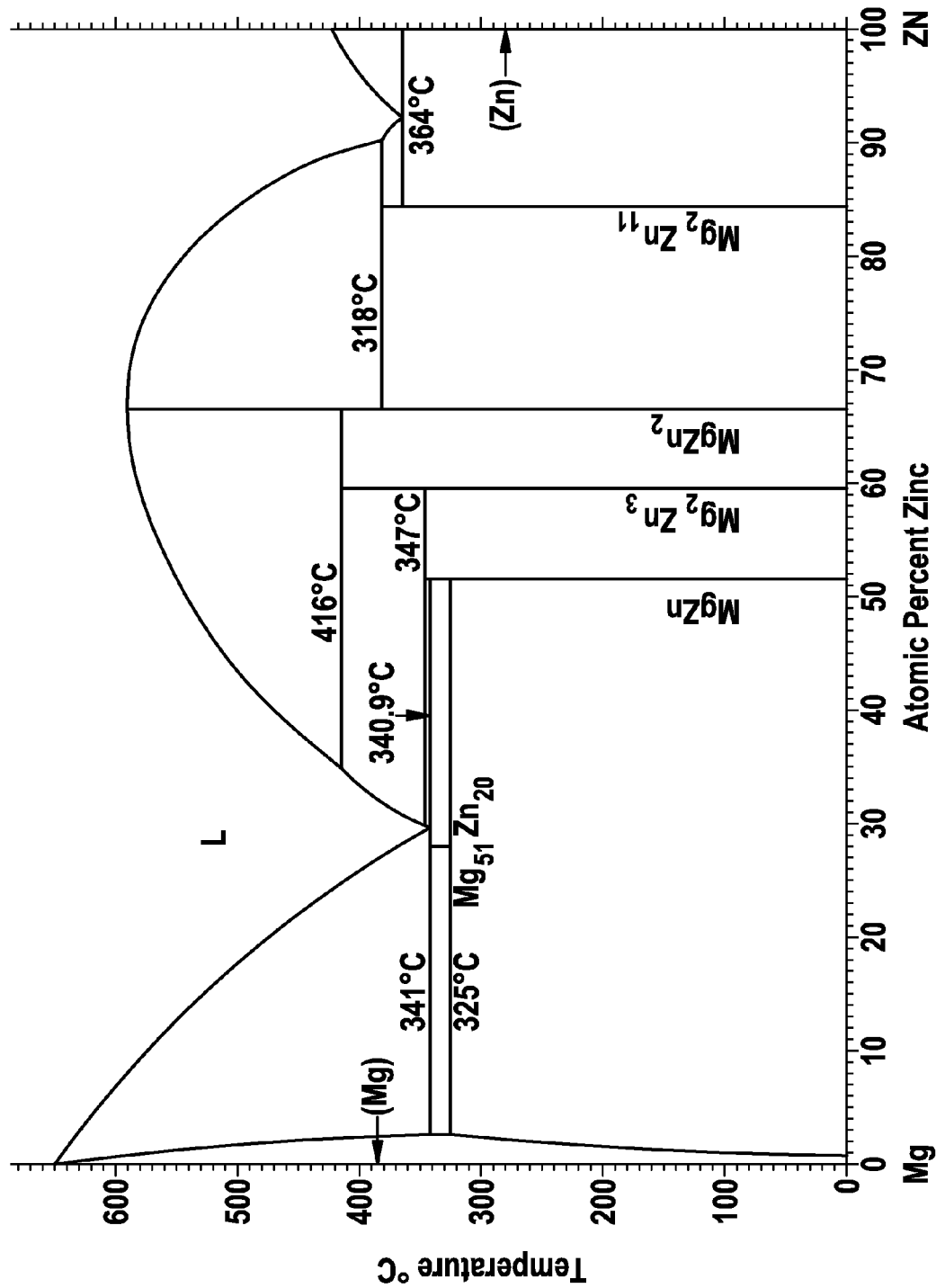
FIG. 5 shows the binary state diagram of the system magnesium-zinc.
Figure 6:
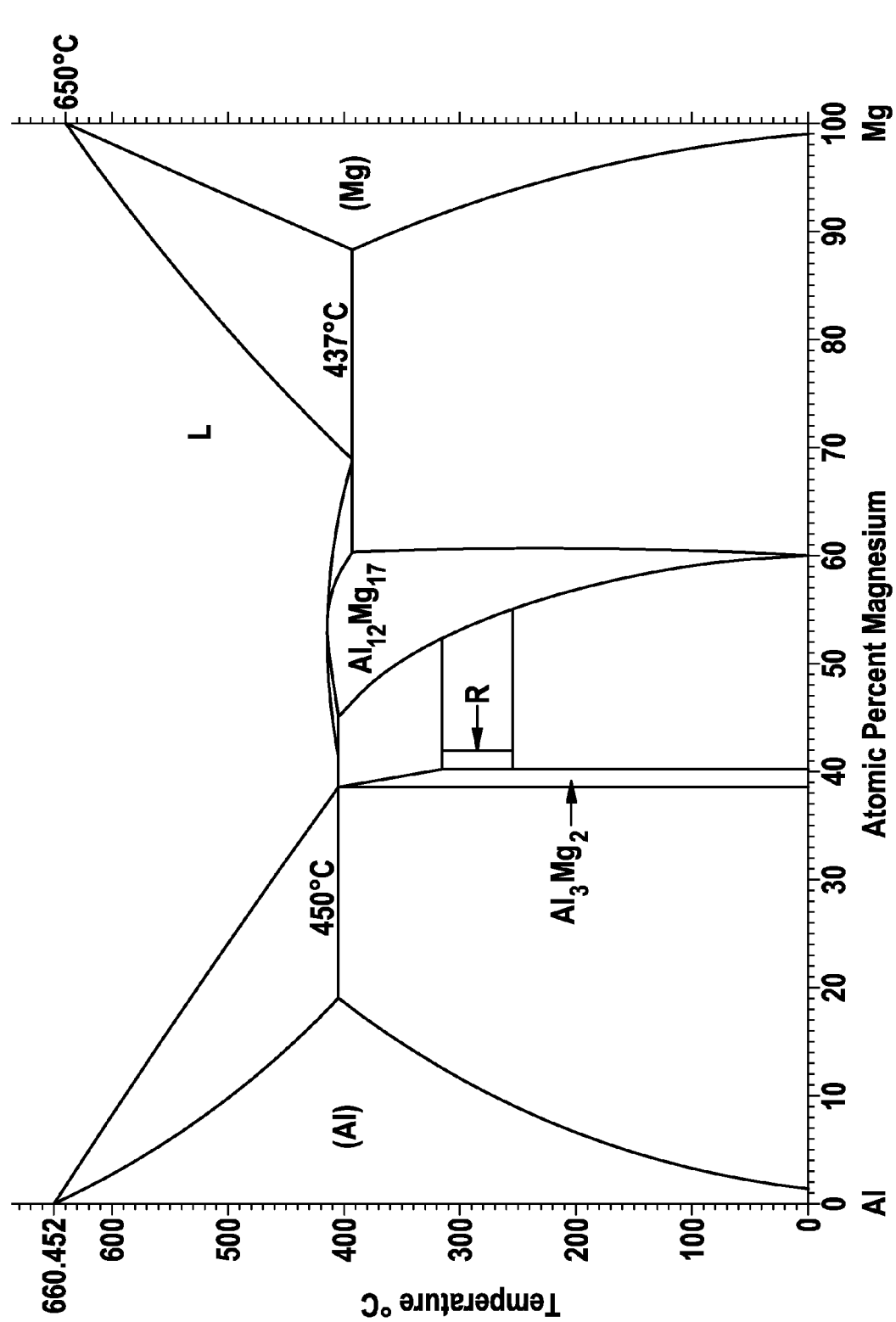
FIG. 6 shows the binary state diagram of the system magnesium-aluminum.

The binary state diagrams illustrated in the FIGS. 5 and 6 include also the phase equilibriums in the process temperature range between 300° C. and 500° C. which visualize the solubility behavior between the different sleeve materials. The state diagram shown in FIG. 5 in which atom % zinc is plotted on the x-axis is mainly relevant for the interface between the sleeve 11 and the sleeve 13, and the state diagram illustrated in FIG. 6 with the concentration of Mg in atom % plotted on the x-axis is relevant for the interface between sleeve 11 and sleeve 12 and describes the solubility behavior in the specified temperature range for the mentioned elements.

After the extrusion step, the semifinished part 20 has a length of 70.8 mm. The second layer 22 generated from the second sleeve 12 has an outer diameter Da2 of 2 mm and a thickness of 56 µm, the first layer 21 generated from the first sleeve 11 has an outer diameter of 1.888 mm and a thickness of 64 µm, and the inner third layer 23 generated from the third sleeve 13 has an outer diameter of 1.76 mm, an inner diameter Dig of 1.618 mm and a thickness of 71 µm. The total thickness of the wall of the semifinished part 20 is therefore 191 µm.

Subsequently, the extruded semifinished part 20 generated from the sleeve combination 10 is removed from the tool. Now, the semifinished part 20 is subjected to a stress relief annealing step between 300° C. and 500° C. for 1 minute up to 60 minutes under inert gas, for example argon. Then, the semifinished part is cooled to room temperature.

Further process steps are configured analogous to the known and frequently described end stage of the production method for implants and comprise final forming processes such as laser cutting, corundum blasting, deburring, etching and electrolytic polishing. The etching and electrolytic polishing steps can be carried out, e.g., in a solution containing phosphoric acid at room temperature for a period of 0.5 minutes to 4 minutes (preferably 2 minutes). It is in particular to be mentioned that the processes etching, corundum blasting and electrolytic polishing are associated with material removal. For example, the material removal during etching for 2 minutes is between 10 µm and 20 µm of the wall thickness.

Thus, at the end of the production method, the implant, e.g., the stent, still has a total wall thickness of 166 µm, wherein the thickness of the second layer 32 is approximately 41 µm and the thickness of the third layer 33 is approximately 61 μm. The thickness of the first layer 31 arranged therebetween is unchanged with respect to the thickness of the first layer 21 at 64 μm of the semifinished part 20 because the final forming processes preferably act on the outer side of the semifinished part, wherein the material removal on the (outer) shell surface of the semifinished part 20 of approximately 15 μM, for process-related reasons, is slightly greater than the material removal on the inner surface of the semifinished part 20 (approximately 10 μm).

Thus, the outer diameter Da3 of the implant 30 is approximately 1.97 mm and the inner diameter Di3 is approximately 1.638 mm.

Further possibilities for the arranging sleeves into a sleeve combination which, analogous to the above illustrated method, can be formed into a semifinished part and can be further processed into an implant are listed below. Here, the position of the sleeve listed in each case in the first column corresponds to the position shown in FIG. 1.

a) Abluminal Variant 1

| Position of the sleeve | Material | Outer diameter [mm] | Inner diameter [mm] | Resulting wall thickness [μm] |
|---|---|---|---|---|
| 12 | Al99, 5 | 3.925 | 3 | 462 |
| 11 | Mg WE43 | 3 | 1.8 | 600 |

This variant includes a system in which the resulting semifinished part and the implant are structured in two layers, wherein the outer layer is rich in Al. A stent produced according to this variant is characterized with respect to a reference stent made from solid WE 43 by a significantly lower fracture susceptibility. Hereby, in the case of a given stent design and an initial outer diameter of 2 mm, a maximum dilatation diameter of 5 mm without strut fracture can be achieved. In comparison to that, the reference stent would already show first strut fractures at 4.5 mm.

b) Abluminal Variant 2

| Position of the sleeve | Material | Outer diameter [mm] | Inner diameter [mm] | Resulting wall thickness [μm] |
|---|---|---|---|---|
| 12 | ZnAl4 | 3.925 | 3 | 462 |
| 11 | Mg WE43 | 3 | 1.8 | 600 |

From this system, a double-layered semifinished part is produced, wherein the outer layer is rich in Zn and has approximately 4 mass % of Al. A stent produced according to this variant is characterized with respect to a reference stent made from solid WE 43 by a degradation time which is extended by 2 month, i.e. from initially 6 months to now 8 months.

c) Luminal and Abluminal Variants

| Position of the sleeve | Material | Outer diameter [mm] | Inner diameter [mm] | Resulting wall thickness [μm] |
|---|---|---|---|---|
| 12 | Al99, 5 | 3.925 | 3.4 | 262 |
| 11 | Mg WE43 | 3.4 | 2.4 | 500 |
| 13 | ZnAl4 | 2.4 | 1.8 | 300 |

Figure 2:
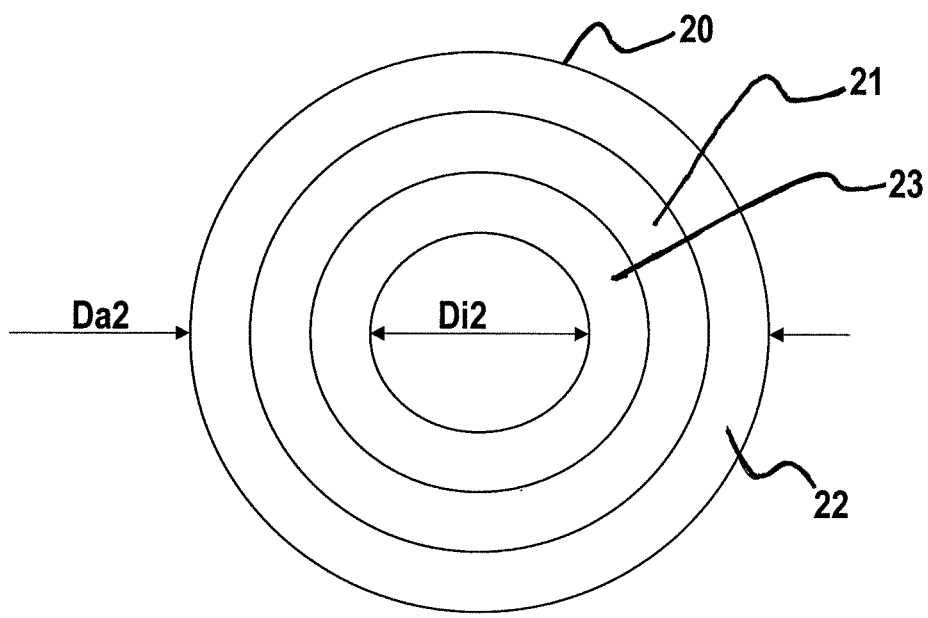
FIG. 2 shows a cross-section though the semifinished part according to the invention after the forming step.
Figure 3:
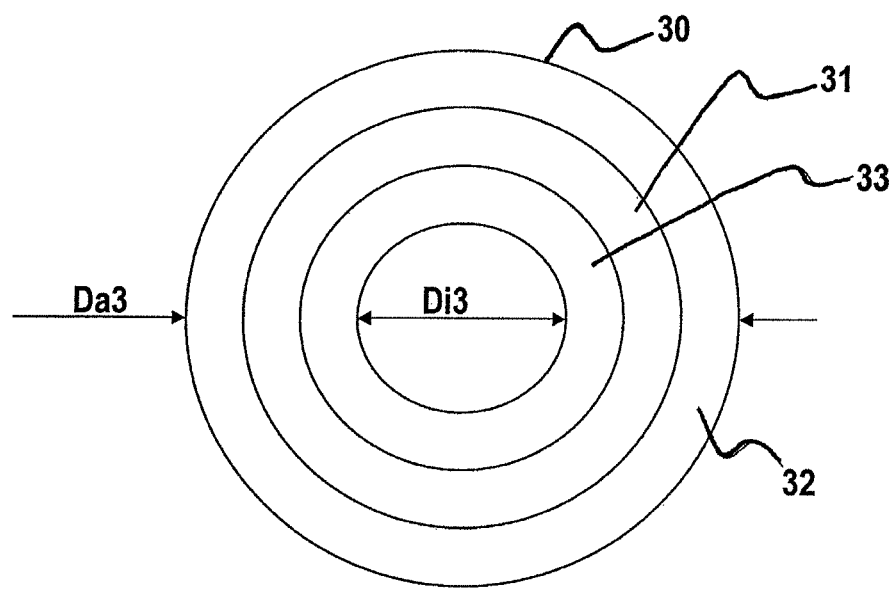
FIG. 3 shows a cross-section through the implant according to the invention after the forming step and further forming process steps.

This combination of the variants a) and b) combines the advantages of lower fracture susceptibility and an extended degradation time. With respect to the reference stent made from solid WE43, a dilatation diameter increased by 0.3 mm and a degradation time extended by 2 months can be achieved. This variant was illustrated above by means of the FIGS. 1 to 3.

d) Luminal Variant 1

| Position of the sleeve | Material | Outer diameter [mm] | Inner diameter [mm] | Resulting wall thickness [μm] |
|---|---|---|---|---|
| 11 | Mg WE43 | 3.925 | 2.4 | 762 |
| 12 | Al99, 5 | 2.4 | 1.8 | 300 |

From this system, a double-layered semifinished part or implant can be produced, wherein the inner layer is rich in Al. A stent produced according to this variant is likewise characterized with respect to a reference stent made from solid WE 43 by a degradation time that is extended by two months.

e) Luminal Variant 2 (Variant for Orthopedic Applications)

| Position of the sleeve | Material | Outer diameter [mm] | Inner diameter [mm] | Resulting wall thickness [μm] |
|---|---|---|---|---|
| 12 | AZ91 | 3.925 | 2.4 | 762 |
| 11 | ZnAl4 | 2.4 | 1.8 | 300 |

From these sleeves, likewise, a double-layered semifinished part or implant is produced, wherein both sleeves contain Zn as well as Al. The alloy AZ91 is a magnesium-based alloy with 9% Al and 1% Zn. The inner layer is rich in Zn with 4% Al. From this semifinished part, in particular small-sized cannulated absorbable bone screws (small fragment screws with an outer diameter of 2 mm) for the treatment of radial fractures can be produced. Said screws have the advantage that they are completely absorbed within 2 years by the surrounding bone. Hereby, a further intervention for removing the implant is no longer required. Further applications are cannulated interference screws for reconstructing ruptured cruciate ligaments. In comparison to today's clinically used screws made from degradable polymers, the mentioned screws are characterized by a higher strength. Because of this, it is possible to work with higher tightening torques so that the process of bone fragment fixation is made easier.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

REFERENCE LIST

10 Sleeve combination
11, 12, 13 Sleeve
20 Semifinished part
21, 22, 23 Layer of the semifinished part 20
30 Implant
31, 32, 33 Layer of the implant
41 Punch
42 Die
43 Outlet of the die
Da1 Outer diameter of the sleeve combination 10

Di1 Inner diameter of the sleeve combination 10
Da2 Outer diameter of the semifinished part 20
Di2 Inner diameter of the semifinished part 20
Da3 Outer diameter of the implant 30
Di3 Inner diameter of the implant 30
F Pressing force

What is claimed is:

1. A method for producing an intraluminal endoprosthesis, comprising:
   a) producing a semifinished part by
      (i) providing a first sleeve from a first metallic material and at least one second sleeve from a second metallic material,
      (ii) arranging the first sleeve and the at least one second sleeve into one another to form a press fit sleeve combination, and
      (iii) extruding the press-fit sleeve combination at an increased temperature to form the semifinished part; and
   b) cutting a grid from the semifinished part using a laser.

2. The method according to claim 1, characterized in that prior to cutting the grid, a tempering step is carried out with the semifinished part for at least 1 minute in a temperature range between 300° C. and 500° C.

3. The method according to claim 1 characterized in that, the at least one second sleeve contains an element selected from the group consisting of aluminum, zinc, and an alloy containing aluminum, and an alloy containing zinc.

4. The method according to claim 1, characterized in that the first sleeve contains magnesium or a magnesium alloy.

5. The method according to claim 1, characterized in that the extrusion is carried out with a tool and with the sleeve combination heated to a range from 300° C. to 500° C.

6. The method according to claim 1, characterized in that the first sleeve is arranged in the at least one second sleeve.

7. The method according to claim 1, characterized in that the at least one second sleeve is arranged in the first sleeve.

8. The method according to claim 1, characterized in that the first sleeve and the at least one second sleeve are first etched and subsequently dried prior to the arranging in one another.

9. The method according to claim 1, characterized in that an outer diameter of the formed semifinished part is not more than 60%, optionally not more than 55% of the outer diameter of the sleeve combination prior to the extrusion.

10. The method according to claim 1, characterized in that a total wall thickness of the formed semifinished part is not more than 25% of a total wall thickness of the sleeve combination, optionally not more than 20% of the total wall thickness of the sleeve combination prior to the extrusion.

* * * * *